United States Patent [19]
Grifka et al.

[11] Patent Number: 6,090,142
[45] Date of Patent: Jul. 18, 2000

[54] HAIRPIECE ATTACHMENT IMPLANT

[76] Inventors: Stephen Grifka, 1360 Allenford Ave., Los Angeles, Calif. 90049; Daniel R. Grifka, 1280 Mill La., San Marino, Calif. 91108

[21] Appl. No.: 09/185,806

[22] Filed: Nov. 4, 1998

[51] Int. Cl.[7] .......................................................... A61F 2/10
[52] U.S. Cl. ............................................. 623/15; 606/187
[58] Field of Search ......................... 623/15, 66; 132/53, 132/56, 201

[56] References Cited

U.S. PATENT DOCUMENTS

| | | |
|---|---|---|
| 3,621,837 | 11/1971 | Gindes . |
| 3,811,425 | 5/1974 | Widdifield . |
| 3,858,247 | 1/1975 | Bauman . |
| 3,862,453 | 1/1975 | Widdifield ................................ 623/15 |
| 3,908,674 | 9/1975 | Kessler . |
| 3,942,195 | 3/1976 | Bauman . |
| 4,037,274 | 7/1977 | Agosta . |
| 4,050,100 | 9/1977 | Barry . |
| 4,054,954 | 10/1977 | Nakayama et al. . |
| 4,265,246 | 5/1981 | Barry . |
| 4,372,317 | 2/1983 | Baumann . |
| 4,676,802 | 6/1987 | Tofield et al. . |
| 4,753,656 | 6/1988 | Tofield et al. . |
| 5,441,540 | 8/1995 | Kim ........................................... 623/66 |
| 5,545,224 | 8/1996 | Israelsen . |
| 5,607,479 | 3/1997 | Jones et al. . |
| 5,643,308 | 7/1997 | Markman . |
| 5,697,979 | 12/1997 | Pignataro ................................. 623/15 |
| 5,741,336 | 4/1998 | Fraser . |

*Primary Examiner*—Mickey Yu
*Assistant Examiner*—Alvin Stewart
*Attorney, Agent, or Firm*—Price Gess & Ubell

[57] ABSTRACT

A hairpiece attachment implant is taught wherein a subdermal base is implanted below the epidermal layer of the scalp and transdermal posts protruding through the scalp's epidermal layer provide nodes for attachment of a hairpiece prosthesis. The implants, which are made of a biocompatible material such as titanium or Crystal Sapphire, preferably comprises a plurality of elongate members connected so as to provide a subdermal base. The transdermal posts are connected to upper surfaces of the elongate members at generally perpendicular angles where the transdermal posts lie partially below the epidermal layer and partially exposed above the epidermal layer. A spherical connector preferably provides a means for releasably attaching the hairpiece to the platform via a ringed connector, or, alternatively, an aperture in the spherical connector provides a point where a ligature on the hairpiece can be tied down.

9 Claims, 2 Drawing Sheets

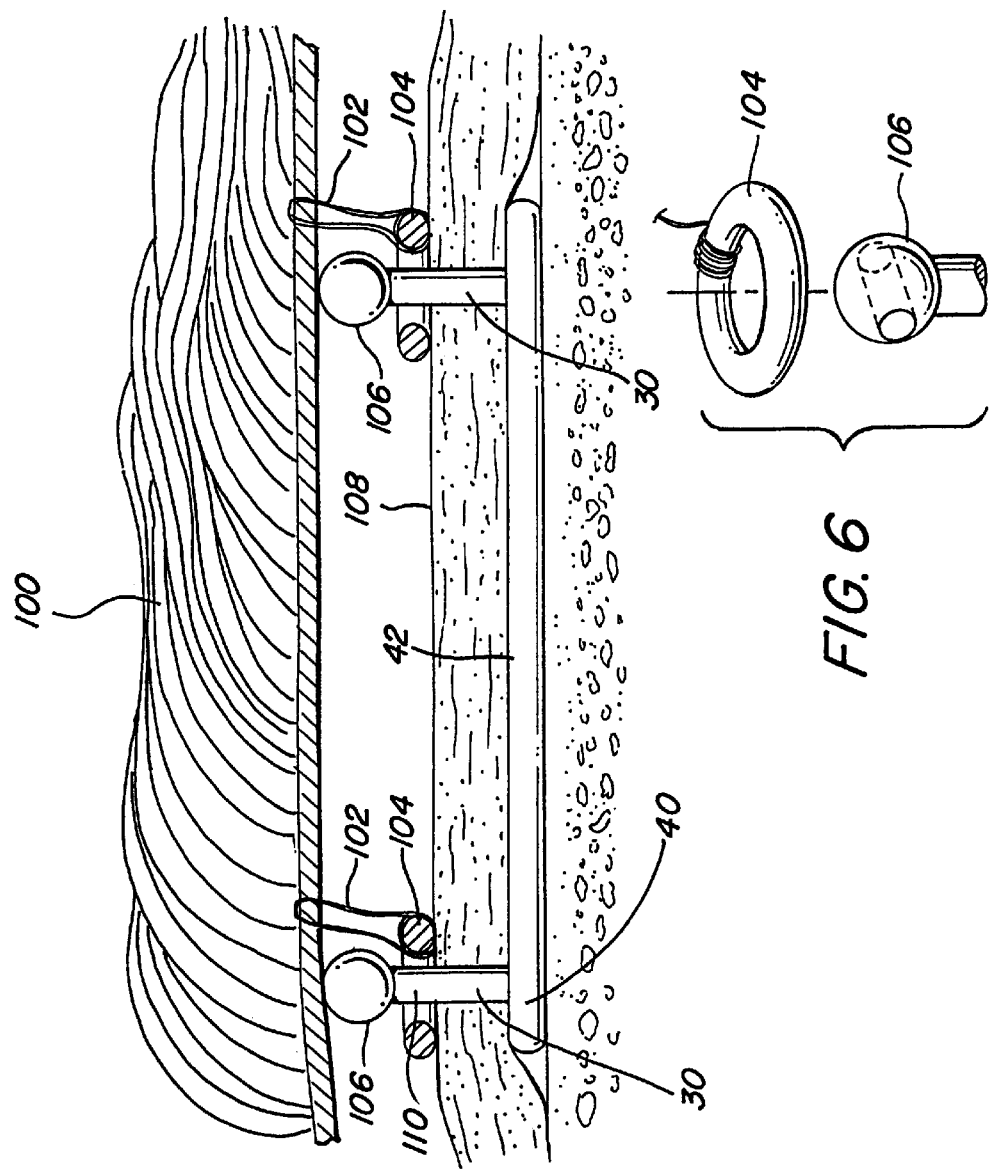

HAIRPIECE ATTACHMENT IMPLANT

BACKGROUND OF THE INVENTION

1. Field of the Invention

The present invention relates generally to the field of prosthesis attachment, and more specifically to an implant for attaching a hairpiece prosthesis to a scalp.

2. Description of Related Art

There are a multitude of applications for affixing a hairpiece to a human scalp comprising both invasive and non-invasive methods and apparatus. Non-invasive methods include adhesives, ties which fasten to existing hair strands, form-fitting materials which adhere to the scalp, and the like. Invasive methods have comprised sutures (see Kessler, U.S. Pat. No. 3,908,674), implanted magnets (see e.g. Fraser, U.S. Pat. No. 5,741,336), cranial fasteners (see Israelsen, U.S. Pat. No. 5,545,224 and Pignataro, U.S. Pat. No. 5,697,979), and wire implants (Gindes, U.S. Pat. No. 3,621,837). Each of these methods and apparatuses has their distinct advantages and disadvantages. The art is continually striving to produce a safe, effective method of attaching a hairpiece with the flexibility to remove the hairpiece while maintaining a high level of confidence that the hairpiece will not become inadvertently dislodged or misaligned.

SUMMARY OF THE INVENTION

The present invention seeks to overcome the shortcomings of the prior art and provide an effective method of hairpiece prosthesis attachment by utilizing a plurality of subdermal bases implanted below the epidermal layer, each including a transdermal post or plurality of transdermal posts projecting from the bases through the epidermal layer and having an attachment mechanism located at the exposed end of the post(s). The implant base and posts are manufactured from a bio-compatible material such as, for example, Crystal Sapphire or titanium. In a preferred embodiment, the base comprises a T-shaped member with posts disposed at distal positions from the juncture point. This configuration provides a stable platform which resists slipping and improves the stability of the hairpiece. The posts in a preferred embodiment include a spherical end which provides a docking or attachment point for a hairpiece, where a ringed engagement member is pressed over the spherical end to lock the hairpiece to the implant. Alternatively, the spherical end includes an aperture that may be used to tie the hairpiece down, or a combination of both attachment methods may be employed.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures thereof, and wherein:

FIG. 4 is a cut-away side view of the present invention after insertion of the subdermal base below the epidermal layer, and further illustrating the cooperation of the spherical connector and mating ring receiver in a locking relationship;

FIG. 5 is an elevated, perspective view of another preferred embodiment illustrating a method of attaching a hairpiece to the implant comprising a ligature used to tie down the hairpiece; and FIG. 6 is an enlarged, perspective view of the spherical connector and mating ring receiver illustrating the attachment method.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an attachment implant for securing a hairpiece prosthesis to a human scalp in a reliable and comfortable manner.

Figure 1:
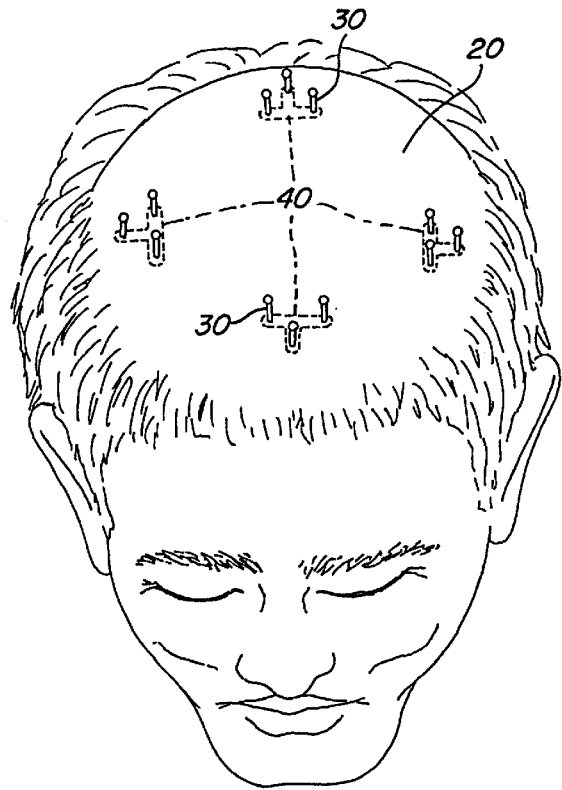
FIG. 1 is an elevated view of a plurality of hairpiece attachment implants of the present invention wherein a plurality of transdermal posts are projecting from a set of hidden subdermal bases.

FIG. 1 illustrates a portion of a human scalp 20 where significant hair loss has taken place. The hairpiece attachment implant of the present invention provides a docking means to support and secure a hairpiece to the region of the scalp at the periphery of the hair loss. The attachment is achieved in a multinodal embodiment by a plurality of implants 40 (shown as dashed lines in FIG. 1) each comprising three transdermal posts 30. The implants are surgically inserted below the scalp's epidermal layer such that the transdermal posts 30 protrude through the epidermal layer and are exposed above the scalp's surface. The number and arrangement of the subdermal implants will vary with each case and will be related to the number of implants deemed necessary to secure a hairpiece in each specific case.

Figure 2:
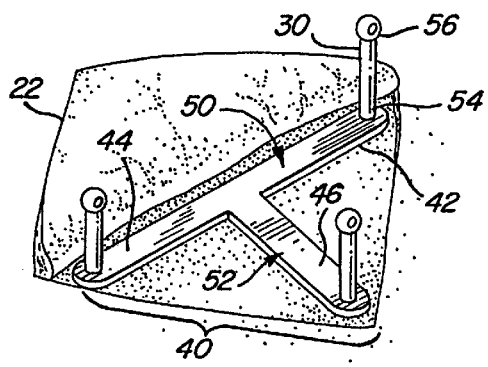
FIG. 2 is an elevated, perspective view of a multinodal embodiment of the present invention illustrating the cut-away of the epidermal layer and the placement of the hairpiece attachment implant.

Turning to FIG. 2, a preferred embodiment of hairpiece attachment implant 40 of the present invention is illustrated wherein a subdermal base 42 comprises a T-shape. Initially, a V-shaped incision in the scalp is made and the epidermal layer 22 is peeled back exposing the periosteal layer. The T-shaped subdermal base 42 comprises a first elongate member 44 and a transverse elongate member 46 connected to its center 48 and projecting laterally therefrom. Each elongate member 44,46 has generally flat upper surface 50,52 and lower surface to minimize the disturbance on the surface of the scalp. Attached to the elongate member 44 at distal ends is a transdermal post 30. The T-shaped design of the subdermal base 42 allows the transdermal posts 30 to be spaced apart on the periphery and covers more area on the scalp. Each subdermal post 30 is comprised of a first end 54 which connects to the subdermal base 42 below the scalp epidermal layer, and a second end 56 which is disposed above the scalp epidermal layer after the insertion of the subdermal base 42 is complete. The implant 40 is made of a biocompatible material such as, for example, titanium or Crystal Sapphire.

Figure 3:
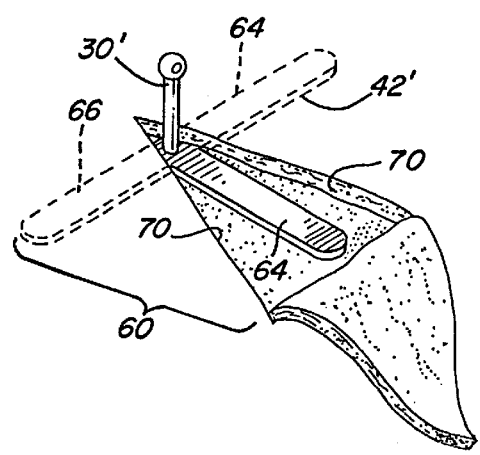
FIG. 3 is an elevated, perspective view of a single node embodiment of the present invention.

FIG. 3 illustrates a uninodal implant embodiment 60 of the present invention on a T-shaped subdermal implant 42'. The elongate members 64 project radially from the center point 66 to form the T-shaped subdermal base 42' and are preferably longer than the height of the transdermal post 30' to increase the stability of the implant 60. The transdermal post 30' is also located at the center point 66 where the radially connected elongate members 64 meet. As can be appreciated, in FIG. 3 the T-shaped subdermal base 42' is positioned under the epidermis after performing the V-shaped incision such that the placement of the elongate members 64 is not directly underneath the incision lines 70. This allows for improved healing without tension in the epidermal layer and further leads to a substantial decrease in the possible complications of scars or extrusion or slippage of the implants.

Turning to FIG. 4, a cut-away side view is presented wherein a hairpiece 100 is attached to the hairpiece attachment implant 40 after the implant has been surgically implanted. The hairpiece 100 comprises a tether 102 at specified locations which is connected to a ringed mating receiver 104. The ring receiver 104 is sized to snugly fit over a spherical connector 106 on the upper end of the transdermal post 30. The hairpiece 100 is attached by popping each ring receiver 104 over the spherical connector 106 in such a manner that the force required to remove the ringed receiver 104 is greater than that which is expected under normal use of the hairpiece. As can be seen in FIG. 4, the subdermal base 42 is orientated generally parallel to the upper surface of the scalp 108. The transdermal posts 30 comprise a cylindrical section 110 which is attached at one end to the subdermal base 42 and includes an exposed portion above the upper surface of the scalp 108 at the second end of the transdermal post 30. It is the second end of the transdermal post 30 at which the spherical connector 106 is attached (see FIG. 6).

FIGS. 5 and 6 illustrate two alternate attaching embodiments for the hairpiece attachment implant. In FIG. 5, the spherical connector 106 includes an aperture 120 which passes completely through. The hairpiece 100 is provided with a tether or ligature 122 which is passed through the aperture 120 and securely tied thereto. In this manner, the hairpiece can be tied as tightly or loosely as desired and provides a releasable connection to the implant. In FIG. 6, the ringed receiver 104 is press-fit over the spherical connector 106 as described above is illustrated in more detail. Either of the two attachment methods or both combinations can be used. The actual method of attachment can take many other forms as is known in the art, and the specific mode of attachment should not be limited to those described above, which are provided as examples only. For example, snap, buttons, clasps and other means of releasably securing two mating elements can be used, and the method of attachment should not be limited to those shown and described above.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A hairpiece attachment implant comprising:
    a subdermal base for surgical insertion below a scalp epidermal layer, said subdermal base comprising a plurality of at least three elongate, radially projecting members emanating from a central point;
    a plurality of transdermal posts each having first and second ends, said first end mounted to said subdermal base below said scalp epidermal layer and said second end disposed above said scalp epidermal layer, wherein said transdermal posts are located at a distal end of said elongate, radially projecting members, and where a length of said radially projecting members is greater than a length of said transdermal posts; and
    an attachment means located at said second end of said transdermal post for securing a hairpiece thereto.

2. The hairpiece attachment implant of claim 1 wherein said attachment means provides releasable attachment to said hairpiece.

3. The hairpiece attachment implant of claim 2 wherein said attachment means comprises a spherical connector at said second end of said transdermal post, said spherical connector adapted to cooperate with a mating ring receiver on said hairpiece such that said hairpiece can be releasably attached by pressing said ring receiver over said spherical connector in a locking relationship.

4. A multi-nodal hairpiece attachment implant comprising:
    a subdermal base including a plurality of at least three elongate members having generally flat upper and lower surfaces and said elongate members each projecting radially from a common connection center; and
    a plurality of transdermal posts each uniquely disposed at a distal end of one of said elongate members on its respective flat upper surface, and projecting generally perpendicular thereto, each of said transdermal posts comprising a cylindrical portion attached at a first end of one of said elongate members where said attachment is located below an epidermal layer when said multi-nodal hairpiece attachment implant is inserted, and said transdermal post further comprising an exposed portion protruding through said epidermal layer where said exposed portion includes means for connecting a hairpiece to said attachment implant.

5. The multi-nodal attachment implant of claim 4 further comprising a spherical connector located at an end of the exposed portion of said transdermal post, said means for connecting a hairpiece to said attachment implant comprising said spherical connector sized to cooperate with a mating ring receiver on the hairpiece to releasably connect said mating ring connector to said spherical connector.

6. The multi-nodal attachment implant of claim 4 further comprising an aperture located at an end of the exposed portion of said transdermal post, said means for connecting a hairpiece to said attachment implant comprising said aperture where a ligature located on said hairpiece is passed through said aperture and tied securely to the transdermal post.

7. A multi-nodal hairpiece attachment system comprising:
    a plurality of subdermal bases each including a first elongate member having generally flat upper and lower surfaces, and a transverse elongate member protruding laterally from said first elongate member at a midpoint thereof and having generally flat upper and lower surfaces, said first elongate member and said transverse elongate member forming a T-shaped subdermal support; and
    a first transdermal post disposed at a distal end of said transverse member on said flat upper surface and projecting generally perpendicular thereto, and second and third transdermal posts each disposed on opposite ends of the upper surface of said first elongate member and projecting generally perpendicular thereto, said first, second, and third transdermal posts each comprising a cylindrical portion attached at a first end to one of the first elongate member and the transverse member, and said first, second, and third transdermal posts each further comprising an exposed portion protruding through said epidermal layer where said exposed portion includes means for connecting a hairpiece thereto.

8. The multi-nodal attachment system of claim 7 further comprising a spherical connector located at an end of the exposed portion of said transdermal post, said means for connecting a hairpiece to said transdermal posts comprising said spherical connector sized to cooperate with a mating ring receiver on the hairpiece to releasably connect said mating ring receiver to said spherical connector.

9. The multi-nodal attachment system of claim 7 further comprising an aperture located at an end of the exposed portion of said transdermal post, said means for connecting a hairpiece to said transdermal posts comprising said aperture where a ligature located on said hairpiece is passed through said aperture and tied securely to the transdermal post.

* * * * *